United States Patent
Greenway et al.

(10) Patent No.: US 6,417,231 B1
(45) Date of Patent: *Jul. 9, 2002

(54) METHOD AND COMPOSITION FOR DELIVERING THERAPEUTICALLY EFFECTIVE AMOUNTS OF PYRUVATE TO A MAMMAL

(76) Inventors: Frank L. Greenway, 376 Shady Lake Pkwy., Baton Rouge, LA (US) 70810; Jennifer C. Rood, 3221 Twelve Oaks Ave., Baton Rouge, LA (US) 70820

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/992,852

(22) Filed: Dec. 18, 1997

Related U.S. Application Data

(60) Provisional application No. 60/033,877, filed on Dec. 23, 1996.

(51) Int. Cl.$^7$ .............................................. A61K 31/22
(52) U.S. Cl. ....................... 514/546; 514/529; 554/123; 554/115
(58) Field of Search ................................ 514/546, 529; 554/123, 115

(56) References Cited

U.S. PATENT DOCUMENTS

| | | | |
|---|---|---|---|
| 4,401,827 A | 8/1983 | de Witt .......................... 560/1 |
| 4,874,790 A | 10/1989 | Stanko ........................ 514/557 |
| 4,981,687 A | 1/1991 | Fregly et al. ................ 424/439 |
| 5,089,477 A | 2/1992 | Fregly et al. .................. 514/23 |
| 5,093,044 A | * | 3/1992 | Wretlind et al. ......... 260/410.7 |
| 5,100,677 A | 3/1992 | Veech ........................ 424/677 |
| 5,134,162 A | * | 7/1992 | Stanko ........................ 514/557 |
| 5,147,650 A | 9/1992 | Fregly et al. ................ 424/439 |
| 5,236,712 A | 8/1993 | Fregly et al. ................ 424/439 |
| 5,238,684 A | 8/1993 | Fregly et al. ................ 424/439 |
| 5,256,697 A | 10/1993 | Miller et al. ................. 514/625 |
| 5,283,260 A | 2/1994 | Miller et al. ................. 514/563 |
| 5,294,641 A | 3/1994 | Stanko ........................ 514/540 |
| 5,531,681 A | 7/1996 | Walton et al. ................. 604/83 |
| 5,531,734 A | 7/1996 | Geckle et al. ........... 604/890.1 |
| 5,533,973 A | 7/1996 | Piontek et al. ................. 604/83 |
| 5,536,751 A | 7/1996 | Bunger ........................ 514/557 |

OTHER PUBLICATIONS

J.W. Bailey et al., "Triacetin: A Potential Parenteral Nutrient," *J. Parental and Enteral Nutrition*, vol. 15, pp. 32–36 (1991).

M. Saroja et al., "A Convenient Method of Esterification of Fatty Acids. Preparation of Alkyl Esters, Sterol Esters, Wax Esters and Triacyglycerols," *Synthetic Communications*, vol. 16, pp. 1423–1430 (1986).

\* cited by examiner

*Primary Examiner*—Dwayne C. Jones
(74) *Attorney, Agent, or Firm*—John H. Runnels

(57) ABSTRACT

A method and composition are disclosed for administering pyruvate in high doses to mammals, including humans. The method and composition do not produce an excessive acid load, salt load, or nitrogen load. Bioavailability of pyruvate from the composition is high. The composition has been named "tripyruvin" (tripyruvyl glycerol, or glycerol tripyruvate), and has the following structure:

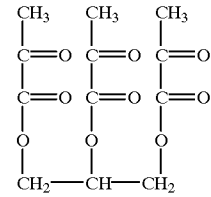

15 Claims, No Drawings

METHOD AND COMPOSITION FOR DELIVERING THERAPEUTICALLY EFFECTIVE AMOUNTS OF PYRUVATE TO A MAMMAL

The benefit of the Dec. 23, 1996 filing date of provisional application 60/033,877 is claimed under 35 U.S.C. § 119(e).

This invention pertains to a method and composition for delivering pyruvate to a mammal.

Pyruvate (2-oxo-propanoate), or its acid form pyruvic acid (2-oxo-propanoic acid), has many potential therapeutic uses.

Beneficial effects that have been reported for pyruvate or pyruvic acid include the following, among others: increasing athletic endurance up to 20%, reducing serum glucose in diabetics, reducing serum lipids and fat deposition, treating alcoholic "fatty" liver, reducing obesity while maintaining lean body tissue, acting as an anti-oxidant, preventing cataracts, improving cardiac function, protecting the heart or intestine from ischemia and reperfusion injury, reversing insulin resistance, inhibiting the growth of breast cancer cells, preventing neuropathy associated with some neurotoxins such as DDC (used in treating HIV infections), improving wound healing, preventing oxalate kidney stones, and treating hyperkeratotic skin lesions.

A major obstacle to many potential uses of pyruvate has been the lack of an effective, non-toxic vehicle to deliver pyruvate to the body at the levels needed for therapeutic effects. Therapeutic effects have typically been reported at levels of 7% to 20% of total dietary calories. Pyruvic acid itself is toxic at such levels, because it presents far too large an acid load to the digestive tract. Nor are soluble salts of pyruvic acid acceptable at such levels, because they produce electrolyte loads well above safe levels.

Prior approaches have included substituting dihydroxyacetone for some of the pyruvate, or administering the pyruvate as an amino acid conjugate such as pyruvyl-glycine. Dihydroxyacetone is inferior to pyruvate in producing beneficial metabolic changes. Pyruvyl-glycine is unacceptable because the required amount would include a nitrogen equivalent of more than half of normal daily protein intake.

U.S. Pat. No. 5,536,751 discloses several demonstrated and proposed, desirable metabolic roles of pyruvate, including the following: (1) raising cytoplasmic phosphorylation potential, increasing the free energy available to a cell; (2) immediate substrate of and autocatalytic agent for pyruvate dehydrogenase, leading to increased availability of NADH to mitochondria, improving a cell's ability to adapt promptly to changing energy demands; (3) immediate substrate of pyruvate carboxylase, which maintains the small concentration of mitochondrial oxaloacetate, which is important in the citric acid cycle and in maintaining ATP synthesis and cellular energy status; (4) by its effect on lactate dehydrogenase, pyruvate can help prevent accumulation of $NADH_2$, which can be hazardous to heart mitochondria; (5) preventing the accumulation of free ferrous ion during ischemia-acidosis/reperfusion, which in turn can reduce the concentration of damaging free radicals produced by the catalytic effect of ferrous ions in the Fenton reaction; (6) several mechanisms for metabolic removal of intracellular hydrogen ions (as opposed to buffering or neutralization); (7) protection of labile but essential —SH groups on various important enzymes and other compounds from free-radical oxidative stress; (8) non-enzymatic neutralization of hydrogen peroxide; and (9) improving blood oxygen transport. Despite the recognition of these multiple physiological roles for pyruvate, the only compositions disclosed by the U.S. Pat. No. 5,536,751 patent for administering pyruvate are the acid and salt forms, generically described as R—C(O)(CO)OH, or a pharmaceutically acceptable salt. However, the only specific embodiments mentioned among that patent's many examples were salts of pyruvic acid such as sodium pyruvate.

U.S. Pat. No. 5,533,973 describes an apparatus and method for modifying a liquid enteral nutritional product during delivery. Included as part of a list of possible nutrients to be administered with the apparatus were "pyruvate precursors such as pyruvamide, or pyruvyl-amino acids, such as, pyruvyl-glycine, pyruvyl-alanine, pyruvyl-leucine, pyruvyl-valine, pyruvyl-sarcosamine and their amides, esters and salts." See similarly U.S. Pat. Nos. 5,531,734; and 5,531,681.

U.S. Pat. No. 5,256,697 describes a method for administering pyruvate to a mammal with a pyruvate precursor in the form of a pyruvamide or a pyruvyl-amino acid, such as pyruvyl-glycine, pyruvyl-alanine, pyruvyl-leucine, pyruvyl-valine, pyruvyl-isoleucine, pyruvyl-phenylalanine, pyruvyl-proline, pyruvyl-sarcosine, their amides, esters, and salts. See similarly U.S. Pat. No. 5,283,260.

U.S. Pat. No. 4,874,790 describes treating animals with diabetic tendencies by oral administration of pyruvate and dihydroxyacetone.

U.S. Pat. No. 5,134,162 describes a process for lowering the blood cholesterol of hyperlipidemic patients by oral ingestion of pyruvate and a confection (cereal bar, fruit bar, candy) containing pyruvate.

U.S. Pat. No. 5,294,641 describes a method for treating a patient prior to or during heart trauma by administering pyruvate orally or intravenously. The disclosure states that the pyruvate may be in the form of organic salts such as calcium or sodium pyruvate, or esters of pyruvic acid such as ethyl amino pyruvate.

U.S. Pat. Nos. 4,981,687; 5,089,477; 5,147,650; 5,236,712; and 5,238,684 disclose compositions and methods to reduce or prevent adverse physiological effects of physical exercise or environmental exposure, or to ameliorate adverse physiological effects of blood loss. The compositions may include glycerol or an ester of glycerol, or pyruvate, or both glycerol and pyruvate.

U.S. Pat. No. 5,100,677 describes processes and compositions for accomplishing fluid therapy with various anions, including pyruvate, or the acid forms, including pyruvic acid.

U.S. Pat. No. 4,401,827 describes acyl derivatives of β-hydroxy-γ-butyrobetaine such as pyruvyl carnitine hydrochloride for use as therapeutic agents in the treatment of cardiac disorders, hyperlipidaemias, and hyperlipidproteinaemias.

J. W. Bailey et al., "Triacetin: A Potential Parenteral Nutrient," *J. Parental and Enteral Nutrition*, vol. 15, pp. 32–36 (1991) discloses infusing dogs with triacetin, the triglyceride of acetate, to provide calories without any resulting overt acute toxicity. Administering triacetin was observed to reduce circulating pyruvate levels.

A novel method and composition have been discovered for administering pyruvate in high doses to mammals, including humans. The novel method and composition do not produce an excessive acid load, salt load, or nitrogen load. Bioavailability of pyruvate from the novel composition is high. The novel composition has been named "tripyruvin" (tripyruvyl glycerol, or glycerol tripyruvate), and has the following structure:

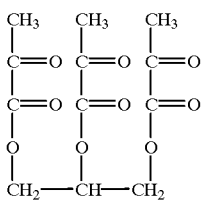

Tripyruvin is about 86% pyruvate by weight.

The novel method comprises administering tripyruvin to a mammal in therapeutic amounts, preferably by oral administration. Even with a consumption sufficient to produce therapeutically effective levels of pyruvate, tripyruvin does not produce a concomitant acid load, salt load, or nitrogen load in the recipient.

Synthesis of Tripyruvin

The synthesis of tripyruvin was a modification of the method of M. Saroja et al., "A Convenient Method of Esterification of Fatty Acids. Preparation of Alkyl Esters, Sterol Esters, Wax Esters and Triacylglycerols," *Synthetic Communications*, vol. 16, pp. 1423–1430 (1986). Briefly, bromine was combined with pyruvic acid to form pyruvyl bromide. Pyruvyl bromide was condensed with glycerol to form tripyruvin, which was then purified through a series of extractions, and concentrated by lyophilization. Tripyruvin was then separated from residual free pyruvate by passage through a strongly basic anion exchange column.

Step 1. Fifty mL methylene chloride were placed in a 125 mL flask. Triphenylphosphine (7.86 g, 0.03 M) was added with stirring by a magnetic stir bar. Bromine was added dropwise until a faint yellow color persisted.

Step 2. Fifty mL methylene chloride were placed in a second 125 mL flask. Pyruvic acid (2.64 g, 0.03 M) was added to the flask, followed by 10 mg sodium hydrogen carbonate. The solution from step 1 was added, and the flask with the mixture was shaken for five minutes. Glycerol (0.92 g, 0.01 M) was added to the flask, and the flask was stirred for fifteen hours with a magnetic stir bar.

Step 3. The solution was poured into a separatory funnel, and extracted with two, 25 mL portions of deionized water. The water was then extracted with two, 25 mL portions of diethyl ether.

Step 4. The water fraction was lyophilized with a rotary evaporator.

Step 5. The synthesized tripyruvin was then present in a mixture with an excess of unreacted free pyruvate. The tripyruvin was separated from free pyruvate by passage through a 1 cm×10 cm column of Dowex™ 1 (Sigma), a strongly basic anion exchange material. The purified tripyruvin was a clear, viscous liquid at room temperature.

After purification, the identity of the tripyruvin was confirmed by laser-desorption mass spectrometry, elemental analysis, and $^1$H nuclear magnetic resonance. Tripyruvin is freely soluble in water.

Bioavailability of Pyruvate from Tripyruvin

The bioavailability to mammals of pyruvate from tripyruvin has been demonstrated in laboratory rats; and will be demonstrated in humans in trials to be performed in accordance with applicable laws and regulations. The basic measurement is the time course of serum pyruvate concentration following oral administration of tripyruvin, compared with that following oral administration of sodium pyruvate or a placebo.

Six male Sprague-Dawley rats, weighing 380±28 grams (mean±standard deviation), were used in the initial animal experiments. The rats were divided into three groups of two rats each, one group of two for the experimental treatment, one group for the conventional sodium pyruvate treatment, and one group for placebo. The rats were housed in hanging wire cages (two per cage) in a room maintained at 22° C., and were kept on a twelve-hour light/dark cycle with lights on at 7 AM. All animals had free access to water and to standard laboratory rodent chow; except that on nights before an experiment food was removed at 6 PM.

An initial time-course experiment was performed with the crude reaction mixture, in which tripyruvin and free pyruvate were both present (i.e., with the product of "Step 4" n the synthesis described above, without the further purification of "Step 5.") 1.14 g of this mixture (76% sodium pyruvate, 24% tripyruvin=0.79 total pyruvate) in 2 mL sterile water was fed by gavage in a single dose. For comparison, rats were fed an equivalent amount of pyruvate as sodium pyruvate in water; or were fed a placebo comprising water only. Blood samples (250 μL) taken from a snipped tail vein were collected before feeding, and at 60, 90, 120, and 150 minutes after gavage feeding.

The assay for serum pyruvate concentration was a modification of the Sigma NADH-NAD assay. Collected blood samples were diluted 1:3 in cold 8% perchloric acid (aqueous), and the precipitates were vortexed and centrifuged. Supernatant (100 μL) was pipetted into a microtiter plate. Trizma base (25 μL) was pipetted into the plate, followed by 25 μL of aqueous NADH solution (1 g/2.2 mL). The absorbance of the solution at 340 nm was then measured as a baseline. Lactase dehydrogenase (50 μL, 10 U/mL) was then pipetted into the plate, and the plate was incubated at 37° C. for 3–5 minutes. Absorbance at 340 nm was again measured (to assay the extent of the reaction NADH→NAD+H$^+$). Standards and two levels of quality control samples were run with each plate. Results are shown in Table 1 for each of the six rats.

TABLE 1

Time Course of Mean Blood Pyruvate Concentrations for Different Treatments (time in minutes, concentration in mM)

| Time ⇒ Treatment ⇓ | 0 | 60 | 90 | 120 | 150 |
|---|---|---|---|---|---|
| H$_2$O (rat 1) | 0.06 | 0.08 | 0.06 | 0.07 | 0.05 |
| H$_2$O (rat 2) | 0.08 | 0.08 | 0.06 | 0.06 | 0.06 |
| sodium pyruvate (rat 3) | 0.06 | 0.10 | 0.09 | 0.12 | 0.16 |
| sodium pyruvate (rat 4) | 0.07 | 0.07 | 0.07 | 0.12 | 0.12 |
| tripyruvin (24%)/ sodium pyruvate (76%) (rat 5) | 0.08 | 0.19 | 0.12 | 0.11 | 0.15 |
| tripyruvin (24%)/ sodium pyruvate (76%) (rat 6) | 0.06 | 0.09 | 0.12 | 0.13 | 0.10 |

This invention was originally conceived as a way to deliver pyruvate without a high acid load or salt load. Table 1 shows that this goal was satisfied. Table 1 also shows an additional, unexpected benefit of tripyruvin: bioavailability of pyruvate was higher from tripyruvin than from sodium pyruvate. Note particularly the more rapid rise in blood pyruvate levels in the rats given the tripyruvin.

In subsequent experiments the time course of blood pyruvate concentration is being compared following administration of equal-volume, equivalent-pyruvate doses of (1) purified tripyruvin (i.e., following "Step 5" in the above synthesis), (2) sodium pyruvate, and (3) calcium pyruvate; compared to (4) sterile water or glycerol placebos. Thirty-two male Sprague-Dawley rats are being used in these experiments, each weighing between 200 and 250 grams. The rats are divided into four groups of eight rats each, one group of eight for the experimental treatment, one for the conventional sodium pyruvate treatment, one for the conventional calcium pyruvate treatment, and one for placebo. The rats are housed in hanging wire cages (two per cage) in a room maintained at 22° C., and are kept on a twelve-hour light/dark cycle with lights on at 7 AM. All animals have free access to water and to standard laboratory rodent chow; except that on nights before an experiment food is removed at 6 PM.

Routes of Administration

Tripyruvin may be administered through a number of routes, which may follow the corresponding routes otherwise generally exemplified, for example, in U.S. Pat. No. 5,536,751 for sodium pyruvate:

1. A pharmaceutical composition containing tripyruvin that also contains a parenteral fluid selected from the group consisting of total parenteral nutritional fluids; kidney and peritoneal dialysis fluids; volume and plasma expanding fluids; pyruvate/acetate near-isotonic solutions; lactate/acetate-free pyruvate isotonic solutions; normal saline solutions; hemoglobin-substitute containing solutions; vitamin supplement products; and cardioplegic solutions.

2. An oral fluid for rehydration with electrolyte balances or rehydration without electrolyte balances comprising a pharmaceutical composition containing tripyruvin.

3. A topical composition selected from the group consisting of medicinal soaps; medicinal shampoos; sunscreens; medicinal ointments; dentrifice; mouthwash; douche solutions; and medicinal baths comprising a pharmaceutical composition containing tripyruvin.

4. An intramuscular injectate selected from the group consisting of an antibiotic and antiphlogistic comprising a pharmaceutical composition containing tripyruvin.

5. A method of using a topical composition comprising tripyruvin and an antibiotic to treat local skin disorders.

6. An aerosolized composition comprising a composition containing tripyruvin, or a composition containing tripyruvin in combination with a bronchodilating agent.

7. A method of using the composition of Feature 6 above to ameliorate or prevent the onset of abnormal conditions caused by a reactive airway disease.

8. A method according to Feature 7 wherein the airway disease is selected from the group consisting of asthma and bronchopulmonary dysplasia.

9. A method of using a perfusion solution containing tripyruvin for isolated animal organs such as the heart, liver, kidney, brain, spleen, vessels, arteries, endothelium, pancreas, and glands.

10. A method of using an incubation solution containing tripyruvin for bacterial or viral cells in culture or cloning studies.

11. A food product capable of enhancing physical endurance, or enhancing other uses of pyruvate, or providing refreshment comprising a pharmaceutical composition containing tripyruvin.

12. A food product according to Feature 11 above wherein said product is a beverage drink.

13. A food product according to Feature 11 above wherein said product is a confectionery food.

14. A food product according to Feature 13 above wherein said product is selected from the group comprising candies or pastries.

15. A vitamin supplement product comprising a vitamin capsule containing thiamine (B1) and tripyruvin.

16. Intravenous solutions: i.v. Ringer's lactate augmented with tripyruvin; i.v. lactate/acetate free Ringer's fortified with tripyruvin; 5% dextrose solution fortified with tripyruvin; or 0.45% sodium chloride solution fortified with tripyruvin.

17. Peritoneal dialysis solutions fortified with tripyruvin, with or without 1–4% dextrose.

18. Hemodialysis solutions fortified with tripyruvin and glucose.

19. Cardioplegic solutions, such as "University of Wisconsin" solution, fortified with tripyruvin.

20. Oral rehydration fluids fortified with tripyruvin.

21. Oil/water ointments fortified with tripyruvin.

22. Emulsifiable ointments fortified with tripyruvin.

23. Injectable antibiotics fortified with tripyruvin.

24. Medicinal aerosols, e.g., for treating asthma, fortified with tripyruvin.

25. Perfusion solutions fortified with tripyruvin.

26. Incubation media fortified with tripyruvin.

27. Cloning media fortified with tripyruvin.

28. Agar culture media fortified with tripyruvin.

29. Refreshments and energizing drinks.

30. Cereal bars and freeze-dried food products.

31. Vitamin capsules.

32. Dentrifice products.

33. Hair care products.

Although tripyruvin is preferred, other esters of pyruvic acid may also be used in the present invention, for example esters of pyruvic acid with ethanol, sorbitol, glucose, mannitol, sucrose, fructose, and other sugars or sugar alcohols.

The complete disclosures of all references cited in this specification are hereby incorporated by reference. In the event of an otherwise irreconcilable conflict, however, the present specification shall control.

We claim:

1. A composition of matter comprising an aqueous solution of tripyruvin.

2. A composition as recited in claim 1, wherein said composition comprises a pharmaceutically acceptable carrier.

3. A food product comprising a composition as recited in claim 1.

4. A food product as recited in claim 3, wherein said product is a beverage.

5. A food product as recited in claim 3, wherein said product is a fluid for oral rehydration.

6. A food product as recited in claim 3, wherein said product is a confectionery, candy, pastry, or cereal bar.

7. An ointment comprising a composition as recited in claim 1.

8. A method of administering pyruvate to a mammal, comprising administering a composition comprising an aqueous solution of tripyruvin to the mammal.

9. A method as recited in claim 8, wherein the composition comprises a pharmaceutically acceptable carrier.

10. A method as recited in claim 8, wherein the mammal is a human.

11. A method as recited in claim 10, wherein the composition comprises a food product.

12. A method as recited in claim 11, wherein the food product is a beverage.

13. A method as recited in claim 11, wherein the food product is a fluid for oral rehydration.

14. A method as recited in claim 11, wherein the food product is a confectionery, candy, pastry, or cereal bar.

15. A method as recited in claim 8, wherein the composition comprises an ointment.

* * * * *